United States Patent [19]

Arnold et al.

[11] Patent Number: 5,383,456
[45] Date of Patent: Jan. 24, 1995

[54] RADIATION-BASED LAPAROSCOPIC METHOD FOR DETERMINING TREATMENT MODALITY

[75] Inventors: Mark W. Arnold, London; Marlin O. Thurston, Columbus, both of Ohio

[73] Assignees: The Ohio State University Research Foundation, Columbus; Neoprobe Corporation, Dublin, both of Ohio

[21] Appl. No.: 214,814

[22] Filed: Mar. 17, 1994

Related U.S. Application Data

[63] Continuation-in-part of Ser. No. 992,617, Dec. 18, 1992.

[51] Int. Cl.6 .......................... A61B 1/04; A61B 6/00; A61B 10/00
[52] U.S. Cl. ..................... 128/653.1; 128/4; 128/654; 128/659; 128/747; 604/26; 604/158
[58] Field of Search ............... 128/753.1, 654, 659, 128/747, 4, 6; 604/104, 23, 26, 158

[56] References Cited

U.S. PATENT DOCUMENTS

| | | | |
|---|---|---|---|
| 4,015,592 | 4/1977 | Bradley-Moore | 128/659 |
| 5,088,492 | 2/1992 | Takayama et al. | 128/659 |
| 5,217,003 | 6/1993 | Wilk | 128/4 |
| 5,261,404 | 11/1993 | Mick et al. | 128/653.1 |
| 5,269,753 | 12/1993 | Wilk | 128/6 |
| 5,301,672 | 4/1994 | Kalender | 128/654 |
| 5,311,859 | 5/1994 | Monroe et al. | 128/6 |

*Primary Examiner*—K. M. Pfaffle
*Attorney, Agent, or Firm*—Mueller and Smith

[57] ABSTRACT

A diagnostic method is described for determining the treatment modality for neoplastic (cancer) tissue within the peritoneal cavity of a patient. The method utilizes a laparoscope with a visual display output as well as a radiation responsive instrument. These instruments are employed first to carry out a visual survey of the colon and then a radionuclide survey of the colon to locate concentrations of radiolabeled locator. A next survey is carried out with the radiation responsive instrument to determine the location of lymph node involvement in the cancer as well as other metastatic disease. Should the latter involvement be found, open laparotomy is indicated as the treatment modality. On the other hand, where no lymph node involvement is determined and the region of locator concentration can additionally be visualized, then conventional laparoscopic resection procedure is the determined treatment modality.

6 Claims, 8 Drawing Sheets

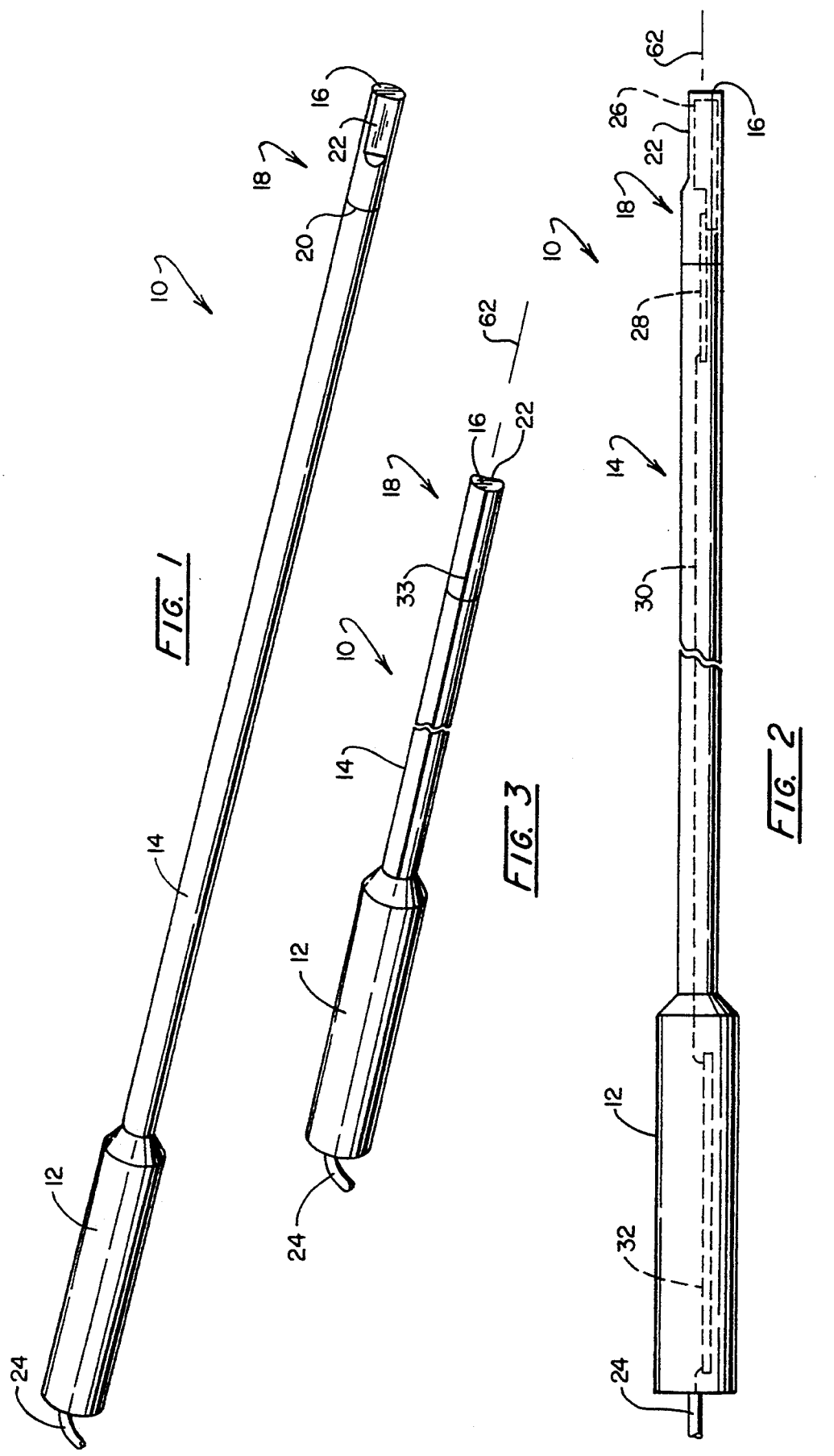

RADIATION-BASED LAPAROSCOPIC METHOD FOR DETERMINING TREATMENT MODALITY

CROSS-REFERENCE TO RELATED APPLICATIONS

This application is a continuation-in-part of application Ser. No. 07/992,617, filed Dec. 18, 1992, entitled "Radiation Responsive Laparoscopic Instrument".

BACKGROUND OF THE INVENTION

Current and historical procedures for the treatment of colon and rectal cancer have been based, for staging purposes, upon the natural history of tumor spread, and thence, upon operative and non-operative options. Operative options generally have looked to the physical location and surgical resection of tumor. A variety of techniques have been brought to bear in the art with the purpose of aiding the surgeon in detecting and localizing neoplastic tissue as part of this surgical procedure. ("Neoplastic tissue", for present purposes, often is referred to as cancerous tissue, though malignant tumor and malignant tumor cells also are found in the terminology of the art. The term "neoplastic tissue" includes all of these.) A substantial amount of effort in aiding the surgeon in locating neoplastic tissue has been through the utilization of radiolabeled antibody for detection purposes. For example, one technique includes the scintillation scanning of patients injected with relatively high energy, e.g. $^{131}I$ labeled antibodies. Such photoscanning or scintillation scanning provides scintigrams difficult to interpret because of blood pool background radioactivity. Computer subtraction of radioactive blood pool agents and the use of two labeled antibodies (one specific for the tumor and one non-specific) have been attempted to enhance imaging. Nevertheless, such techniques have been found to provide little, if any, useful information to the surgeon, especially over and above CAT scans, magnetic resonance imagings, and like traditional techniques. Typically, large tumor is readily located by the surgeon by visualization at the operating theater and, in particular, through palpation, i.e. the feel of a tumor as opposed to that of normal tissue. To achieve operative success, however, it is necessary for the surgeon to somehow locate "occult" tumor, i.e. tumor which cannot be found by the conventional surgical procedure of sight and feel. Failure to locate and remove such occult tumor generally will result in the continued growth of cancer in the patient, a condition often referred to as "recurrent" cancer. In general, conventional diagnostic techniques as, for example, use of the classic gamma camera and the like, fail to find or locate occult tumor. As tumor sites become smaller, the radionucleide concentrations at a given tumor site will tend to be lost, from an imaging standpoint, in the background where blood pool radiation necessarily is present in the patient.

U.S. Pat. No. 4,782,840 by Martin, M.D. and Thurston, Ph.D., entitled "Method for Locating, Differentiating, and Removing Neoplasms, issued Nov. 8, 1988 (the disclosure of which is expressly incorporated herein by reference) reviews such scintillation scanning technique and discloses a much improved method for locating, differentiating, and removing neoplasms. Such technique utilizes a radiolabeled antibody and a portable radiation detection probe which the surgeon may use intraoperatively in order to detect sites of radioactivity. Because of the proximity of the detection probe to the labeled antibody, the faint radiation emanating from occult sites becomes detectable, for example, in part because of the inherent application of the approximate inverse square law of radiation propagation. The procedure is known as the Radioimmunoguided Surgery ™ system (RIGS) (Radioimmunoguided Surgery and RIGS being trademarks of Neoprobe Corporation, Columbus, Ohio) and is successful additionally because of a recognition that tumor detection should be delayed until the blood pool background of circulating radiolabeled antibody has had an opportunity to be cleared from the body. As a consequence, the photon emissions or radiation emitted at minor tumors compared to surrounding tissue becomes detectable in view of the proximity of the probe device to it. Fortuitously, the '840 patent discloses the ability of the radiolabeled antibody to remain bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be determined readily utilizing a hand held probe positioned in close proximity with the tissue tender investigation.

Colonic tumor generally originates at the mucosa or inner layer of the bowel. Because of this interluminal location, i.e. within the interior of the colon, early primary tumor cannot be seen or visualized by the surgeon. Thus, the conventional palpation or "feeling" procedures generally are employed to locate the otherwise hidden neoplasm. Visualization of tumor at the exterior surface of the colon only becomes available as a detection technique when the tumor will have grown or matured to an extent that it extends outwardly through the wall of the colon and, thus, its presence is apparent. One approach to locating the position of essentially hidden tumor or localizing a hidden lesion has been resort to intraoperative colonoscopy. This technique exhibits drawbacks due, in part to a requirement for the insufflation of air into the colon with attendant luminal distension, making subsequent surgery more difficult. In this regard, the technique has a potential for engendering toxicity and breaking the sterile field. Additionally, the added procedure increases anesthesia time, total operating room time, and operative costs.

Tumor which is evidenced or "recurs" following earlier surgery typically is diagnosed by the occurrence of elevating CEA levels (carcinembryonic antigen). Generally, this recurring cancer is, in effect, hidden cancer which was not found in earlier surgery and now has commenced to mature. The carrying out of a second surgical procedure, a procedure sometimes referred to as "second look" surgery, has been the subject of study. A high morbidity rate is associated with such procedure. Often the procedure essentially is an "open and close" one, the patient exhibiting severe metastisis not otherwise detectable and not surgically treatable. This determination of unresectability through open surgery, of course, is attended with severe trauma to the patient.

A highly important aspect of all procedures associated with colorectal and other cancers resides in the proper staging of the patient according to the extent and severity of the disease. Such staging aids in determining the appropriate post-surgical treatment for such patients. Stage I and II patients are believed to be curable by surgery alone, whereas Stage III patients, i.e. patients determined to have cancer spread to the lymph nodes, are treated with some form of post-operative therapy, such as chemotherapy. Stage IV patients, i.e. patients with metastisis to other organs, are treated with a variety of methods, including post-surgical therapy and/or surgical removal of the primary tumor. More severe metastisis typically is not deemed to be treatable by surgery and thus, surgery is not undertaken in order to spare the patients unnecessary trauma. Where the above-noted hidden or occult cancer is not found, residual disease is left behind and is not accounted for with respect to an evaluation of the extent of the disease to determine proper post-surgical therapy.

The contribution of RIGS-based surgery to enhancing the vision-based and touch-based procedures of the surgeon has been substantial. The detection and location approach of this system has permitted the identification and removal of hidden or occult tumor under conditions where otherwise conventional procedures would not have found it. Additionally, the system has been employed in staging, particularly in evaluating lymph nodes and other metastatic disease for staging procedures. The system has been demonstrated in clinical studies to substantially improve the staging of primary colorectal cancer patients which, having been staged by traditional means, were restaged to State III disease based upon the RIGS system as confirmed by pathology findings. As a consequence of such findings, patients so re-evaluated are eligible for post-surgical therapy, such as chemotherapy, resulting in improved patient management. The importance of such staging has been established in view of the National Institute of Health (NIH) consensus report concerning the administration of adjuvant chemotherapy to appropriately stage patients. "NIH Consensus Conference: Adjuvant Therapy for Patients with Colon and Rectal Cancer", JAMA, 1990; 264: 1444–50.

Somewhat recently, laparoscopic surgery (minimal access surgery) has become popular as an alternative to traditional open surgery procedures. Particularly with the development of video-based visual systems, laparoscopic surgical techniques have been employed with more complicated gastro-intestinal procedures. Such procedures look to savings in total health care costs as a result of shorter hospital stays and a more rapid patient return to normal activity. However, these procedures require instrumentation and technique supplanting conventional three-dimensional viewing and tactile feedback to the surgeon. Improved instrumentation particularly is called for where these newer surgical techniques are applied to the detection and removal of neoplastic tissue.

While a variety of laparoscopic instruments have been developed, such equipment falls into two broad categories: those major pieces of equipment that enable the surgeon to perform laparoscopy and those instruments related to the performance of specific tasks or procedures, e.g. electrocautery and laser. Generally, visualization within peritoneal cavity requires "space" in which to shine light and maneuver. In a standard surgical approach or laparotomy this space is created by opening the abdomen and allowing room light and air into the cavity to accommodate three-dimensional viewing. In laparoscopic procedures, this is accomplished by filling the peritoneal cavity with a gas that distends the abdominal wall and provides an area for light and manipulation, a process termed "pneumoperitoneum". Carbon dioxide currently is the standard gas used for pneumoperitoneum. Pneumoperitoneum typically is carried out utilizing an instrument referred to as an insufflator.

Laparoscopic surgery generally features the establishment of one or more portals of entry into the abdominal cavity. Mechanisms for inserting and removing various instruments through these portals without loss of pneumoperitoneum are necessary. These ports are established by the insertion of a trochar tip through the skin of the patient in conjunction with a port defining cannula or sheath. The trocar is inserted through the lumen of the cannula as an obturator. Typically, the cannulas have a spring-loaded trumpet valve to permit the introduction of instruments into the abdomen and prevent gas from escaping. Conventionally, the size of the cannula sleeve is 1 mm larger in diameter than the corresponding instrument that will traverse it. Diameters for such instruments may reach, for example, 15 mm or larger in extent.

Employment of the laparoscopic surgical technique in conjunction with the surgical staging and resection of neoplastic tissue poses limitations heretofore not encountered by the surgeon. With laparoscopic surgical procedures, sight is constrained to the two dimensions available at a video screen and palpation or feel essentially is lost. In effect, the surgeon is maneuvering along or manipulating tissue through elongate instrumentation from a distance of about 18 inches away.

Where a primary tumor has not developed through the wall of the colon or is in regions of the color unaccessible to the camera, it will not be seen by video imaging. Finding this tumor by palpation is not an option available to the surgeon. The constraints associated with lesion demarcation by intraoperative colonoscopy remain, and the procedure often calls upon the surgeon to strategically guess as to tumor location. Where such uncertainty is present, an opportunity for cutting into neoplastic tissue itself is present, a situation representing a potential for peritoneal spread of tumor, or seeding.

The current limitations of laparoscopic or laparoscopic assisted colon surgery also impose severe limitations in carrying out staging of the disease. This again is due principally to the exploratory constraints imposed by the surgical approach wherein lymph node metastisis involvement cannot be adequately evaluated. In this regard, visualization alone of the lymph system using laparoscopic video instrumentation generally will not be achievable, or if achievable will not locate positive or cancerous lymph nodes or other metastatic disease.

Should this minimal access surgery be developed to overcome the above-discussed severe limitations, important advantage may be evolved with the procedure. In this regard, the approach promises a diminished post-operative pain which minimizes the need for narcotic analgesia. The procedure allows patients to resume an oral diet faster, and gives the patient a shorter hospital stay and a more rapid return to normal activities. Some investigators are of an opinion that the incidences of post-operative complications such as atelectasis and pneumonia, deep venis thrombosis, wound infections, and the like are less with the laparoscopic approach.

SUMMARY

The present invention is addressed to a method for determining the treatment modality for patients afflicted with neoplastic tissue (cancer patients). This diagnostic method comprises the steps of administering to the patient an effective amount of radiolabeled locator which specifically binds a marker produced by or associated with neoplastic tissue. Appropriate locators include, for example, antibodies, antibody fragments, single chained antibodies (SCAs), and like substances which selectively accrete at tumor sites. Following such administration, time is permitted to elapse for the radiolabeled locator to preferentially concentrate at any marker located at neoplastic tissue and for unbound radiolabeled locator to be cleared to as to increase the ratio of photon emissions from the marker to background photon emissions in the patient. Thereafter, the peritoneal cavity of the patient is insufflated and access is provided thereto through a plurality of cavity access cannulas. For visualization, a real time laparoscopic camera arrangement is provided with a display. A laparoscopic radiation detection system is provided which includes a base portion engageable by a surgeon, an elongate accessing tube is fixed to the base portion and is dimensioned for slidable insertion through a select one of the cannulas, and has a length along a central axis effective to access neoplastic tissue within the peritoneal cavity. The accessing tube has a passageway extending therethrough and a detector support portion including a window through which photon emissions may pass. A crystal mount is included with the system having a crystal receiving portion positioned at the detector support portion in adjacency with the window. A crystal having a rearward surface supported on the crystal receiving portion to position a forward surface thereof in adjacency with the window is responsive to the photon missions passing through the window to derive an output. A transmission assemblage extending from the crystal through the passageway for transmitting the output is provided and a signal treatment and control assembly is coupled with the transmission assemblage for receiving and electrically treating the output to provide perceptible output signals representing those photon emissions at predetermined count levels above the count levels of background photon emissions. The colon is visually surveyed to the extent possible within the peritoneal cavity by accessing the camera arrangement thereto through a select one of the access cannulas and detecting any visual indication of neoplastic tissue. A radionuclide survey of the colon is carried out within the peritoneal cavity by manipulating the elongate accessing tube of the radiation detection system through a select one of the access cannulas to maneuver the window along and in substantial adjacency with the colon under visualization to the extent possible with the camera arrangement display to detect and differentiate tissue at which the locator has concentrated by correlation of the perceptible output signals to the position of the window with respect to the colon. A radionuclide survey of the lymph nodes is carried out within the peritoneal cavity by manipulating the elongate accessing tube of the radiation detection system through a select one of the cannulas to maneuver the window thereof under visualization at the camera arrangement display to the extent possible into substantial adjacency with lymph nodes to detect and locate a lymph node or other metastatic disease at which the locator has concentrated by correlation of the perceptible output signals to the position of the window. Based upon the above, determination of the treatment modality then is carried out.

Where the patient is diagnosed prior to the noted surveys as presenting neoplastic tissue as primary tumor and the step for visually surveying the colon shows an absence of a visible indication of neoplastic tissue while the step for carrying out a radionuclide survey of the colon has located and differentiated tissue, at which locator has concentrated, and the step for carrying out a radionuclide survey of the lymph nodes locates no lymph node or metastatic disease at which locator has concentrated, then the determination of the treatment modality indicates that a laparoscopically assisted removal of the located and differentiated neoplastic tissue is beneficial as the treatment modality. Thus, the patient will undergo an effective resection of neoplastic tissue with all of the advantages attendant to a minimally invasive surgery.

Where the patient is diagnosed prior to the surveys as presenting neoplastic tissue as primary tumor; and the step for visually surveying the colon shows an absence of a visual indication of neoplastic tissue; and the radionuclide survey of the colon locates and differentiates tissue at which locator is concentrated; and the radionuclide survey of the lymph nodes locates a lymph node at which locator has concentrated, then the determination of the treatment morality indicates that the carrying out of an open laparotomy to remove the located and differentiated neoplastic tissue is beneficial as a treatment modality. Thus, the patient is treated to correct more profound tumor involvement which requires more extensive exploration of the peritoneal cavity with expanded risk which is properly undertaken with open surgical procedures.

Where the patient is diagnosed prior to the surveys as presenting neoplastic tissue as primary tumor; and the step for visually surveying the colon differentiates the tissue at which locator is concentrated; and the radionuclide survey of the lymph nodes locates no lymph node or metastatic disease at which locator has concentrated; then the determination of treatment modality indicates that carrying out a laparoscopically assisted removal of the located neoplastic tissue is beneficial as the treatment modality. As before, such treatment affords the patient the opportunity to gain the advantages of minimally invasive surgery.

Where the patient is diagnosed prior to the surveys as presenting the neoplastic tissue as recurrent tumor; and the radionuclide survey of lymph nodes locates a lymph node or other metastatic disease at which the locator is concentrated; then the determination of treatment modality indicates that a procedure employing surgical resection would not be of benefit to the patient. Thus, the patient is spared the trauma and the risk of major, open surgery which would have no beneficial effect.

Other objects of the invention will, in part, be obvious and will, in part, appear hereinafter. The invention, accordingly, comprises the method possessing the steps which are exemplified in the following detailed disclosure.

For a fuller understanding of the nature and objects of the invention, reference should be had to the following detailed description taken in connection with the accompanying drawings.

BRIEF DESCRIPTION OF THE DRAWINGS

FIG. 1 is a perspective view of a laparoscopic instrument according to the invention;

FIG. 2 is a side view of the instrument of FIG. 1 showing components therein in phantom FIG. 3 is a schematic representation of the instrument of FIG. 1 with the access tube thereof in broken fashion showing an opposite side thereof illustrated;

DETAILED DESCRIPTION

Figure 4:
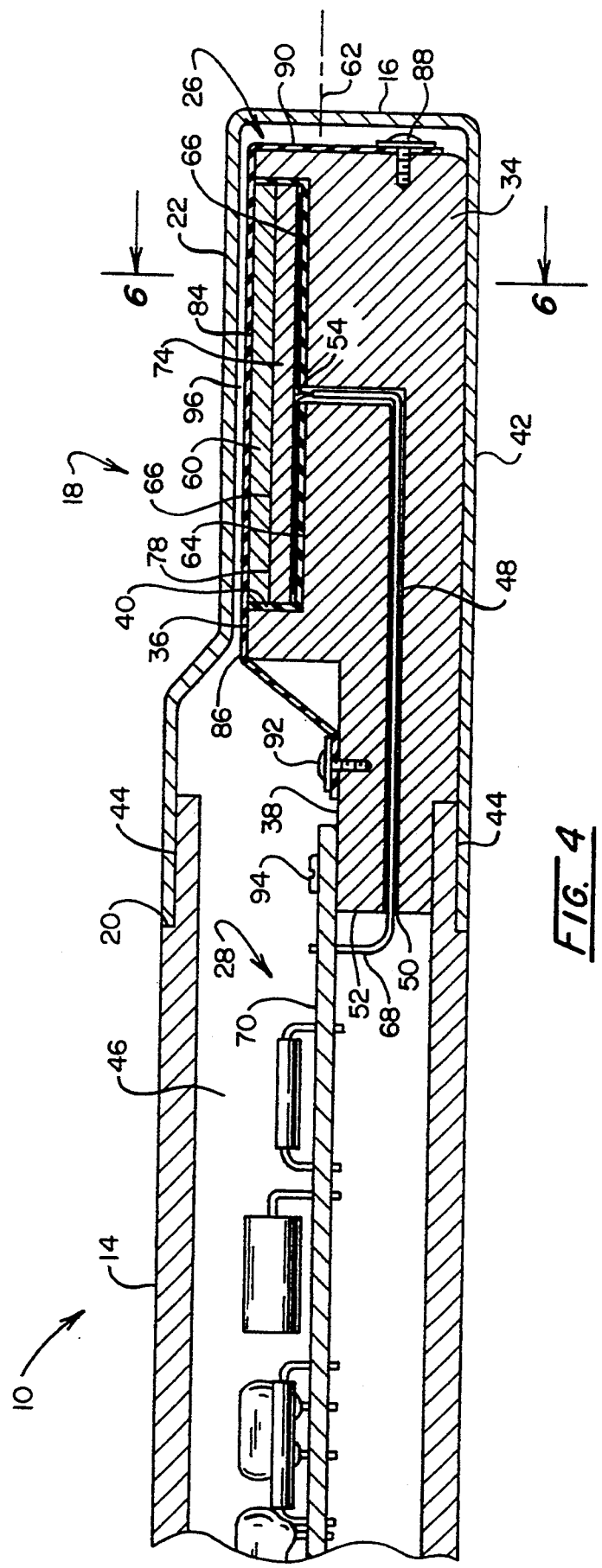
FIG. 4 is a partial sectional view of the instrument of FIG. 1.

The general RIGS procedure commences with the administration to the patient of an effective amount of a radiolabelled locator which specifically binds a marker produced or associated with neoplastic tissue. A "locator" includes a substance which preferentially concentrates at tumor sites by binding with a marker (the cancer cell or product of the cancer, for example) produced by or associated with neoplastic tissue or neoplasms. Appropriate locators today primarily include antibodies (whole and monoclonal), antibody fragments, chimeric versions of whole antibodies and antibody fragments, humanized versions thereof, as well as other tumor specific carriers, i.e. locators. It should be appreciated, however, that single chain antibodies (SCAs such as disclosed in U.S. Pat. No. 4,946,778) and like substances have been developed and they primarily prove efficacious. Biochemistry and genetic engineering may yet produce substances which mimic the function of antibodies in selectively concentrating at sites of neoplastic tissue, though such substances may not be subsumed within the traditional definition of "antibody". "Locator" is a term chosen to include present day antibodies and equivalents thereof, as well as those substances yet to be determined which mimic antibodies in the method of the RIGS system.

An adaptation of radioimmunoguided surgical techniques (RIGS) to laparoscopic procedures involves a need to accommodate a variety of aspects associated with each. The hand-held radiation detecting probe employed conventionally with the RIGS system is described in U.S. Pat. No. 5,070,878 by Denen, issued Dec. 10, 1991, and assigned in common herewith. This probe utilizes a cadmium telluride crystal of adequate surface area which is mounted in a "forward looking" manner. Thus, as the probe is held by the surgeon, the window component thereof at the tip is moved transversely along tissue being evaluated. Because the RIGS surgical approach is one wherein the extent of radiation emanating from a carder located at neoplastic tissue is quite faint, it becomes necessary that the crystal be of adequate surface area to capture sufficient radiation emissions. Of similar importance, because of the rapid fall-off of radiation as the crystal surface is moved away from that tissue region in consequence of the approximate inverse square law of radiation propagation, it is essential that the surgeon maintain a close proximity between the crystal surface behind the probe window and the radioactive tissue. In effect, this application of the inverse square law of radiation propagation aids in sharply delineating the extent or boundaries of neoplastic tissue.

From the laparoscopic surgical standpoint, it is necessary that the laparoscopic instrument be maneuverable, having an access tube or the like of diameter limited by the port of a cannula, for example, about 12 mm. It has been determined that the latter diametric constraint imposes unwanted limitations on the available surface area of a radiation detecting crystal such as cadmium telluride. As a forward looking laparoscopic adaptation of the radiation detecting probe was employed, in addition to the low count rates available with smaller diameter crystals, as the source of radiation was approached, for example in a longitudinal direction along the body cavity, instrument response diminished as the crystal moved across the radiation source because of the shielding positioned about the crystal itself. The laparoscopic instrument intended for radionuclide scanning is required to be configured within the diametric constraints associated with its insertion through a cannula and its anticipated form of maneuvering within the body cavity. Next, the device must be capable of retaining a crystal such as cadmium-zinc-telluride for detection which has adequate surface area to achieve operationally effective radiation detecting sensitivity. This instrument then is called upon to locate neoplastic tissue through faint radiation emissions while being observed, to the extent possible two-dimensionally with a television camera which also is inserted through a cannula into that same body cavity. In effect, the instrument is called upon, inter alia, to replace the surgeon's sense of touch, to support the surgeon's vision, which now is restricted to two dimensions, and to develop RIGS-based information as to the location of cancer involvement.

The methodology described in connection with the present invention is one which employs RIGS technology in conjunction with certain laparoscopic procedures utilized for diagnosis or evaluation of the condition of cancer patients. With the method, trauma otherwise imposed upon a patient by open surgical techniques is avoided through the utilization of radionuclide surveys of certain regions within the peritoneal cavity. An appreciation of the diagnostic technique necessarily calls for a cognizance of the internal structure of the patient.

Because of the anatomical structure of the human body, surgical procedures invading the peritoneal cavity have an anterior influence. Surgically invasive entry into the abdomen is one which encounters what may be considered layered regions commencing with the omentum, an outer protective curtain-like tissue and ending with the backbone and the pelvis. To reach, evaluate, and perhaps resect at successive regions requires manipulation of organs such as the lengthy small bowel to locations away from areas of interest. This conventionally is carried out by retraction as well as by gravity, the latter being accomplished through orientations of the patient's body. As surgical procedures reach deeper into the abdomen, they are accompanied by increasing risk, for example, as cancer involved with tissue is located in proximity to the systems of the aorta and vena cava. As the latter organs are approached, the delicacy of procedure becomes more profound. It also should be borne in mind that the organs encountered in the course of abdominal surgery are not static. In this regard, the terms "dynamic", "slippery" and "sliding" are adjectives appropriate to the description of this task. These accessing conditions encountered by the surgeon become somewhat exacerbated with laparoscopic surgery.

Referring to FIG. 1, a laparoscopic instrument which may be employed with the diagnostic method is revealed in general at 10. Instrument 10 includes a hand-grippable cylindrical base portion 12 to which an elongate accessing tube 14 is fixed. Accessing tube 14 is of a length convenient to the surgeon for accessing those regions of the abdominal cavity intended for neoplastic tissue detection and localization. This length may, for example, be about 14 inches (36 cm) and extends to a tip 16. Inwardly from this tip 16 there is a detector support portion represented generally at 18 which extends to a union or joint represented at line 20. Tube 14 is cylindrical, having an outer diameter, for example, of 11 mm such that it is suitable for insertion through a conventional 12 mm diameter cannula port. This cylindrical configuration extends through to the tip 16, however, the detector crystal mounted within the instrument 10 provides for "side looking" evaluation of impinging radiation. This is through a planar or flat window 22 located at the detector support portion 18 and which is seen to have a somewhat elongate rectangular peripheral shape. The crystal detector which will be seen to be spaced but closely proximate the window 22 is operated in conjunction with signal treatment and control circuitry which ultimately is coupled through a console mounted connector (not shown) to the instrument 10 via a shielded flexible cable 24 extending from the hand-grippable base 12. In general, the control and signal treatment components are contained within a console to which the cable 24 leads and which is located out of the sterile surgical field. However, some signal treatment components may be necessitated at the instrument 10 itself. Looking additionally to FIG. 2, a crystal mount arrangement is shown in general in phantom at 26 located within the accessing tube 14 at the detector support portion 18. Located in adjacency with the crystal mount 26 is a preamplification stage represented generally at 28. Depending upon the constraints of the size of the passageway within tube 14, it may be found appropriate to split the preamplification function of the instrument 10 into two components. Accordingly, a forward stage 28 is positioned in proximity to crystal mount 26 and stage 28 then communicates, for example, with shielded cable as represented by dashed line 30 with a second or final preamplification stage shown in phantom at 32 which is mounted will, in the hand-grippable base 12. Cable 24 is electrically connected with this last amplification stage represented at 32.

Referring to FIG. 3, instrument 10 is seen rotated about its longitudinal axis to reveal a thin line 33 formed, for example, by being engraved and extending along the back surface of accessing tube 14 including the detector support portion 18. This line may be observed by the visual or video portion of laparoscopic instrumentation during surgery. Thus, the surgeon is given visual information as to the orientation of window 22, for example, even though the tip portion 22 is not camera visible.

Figure 5:
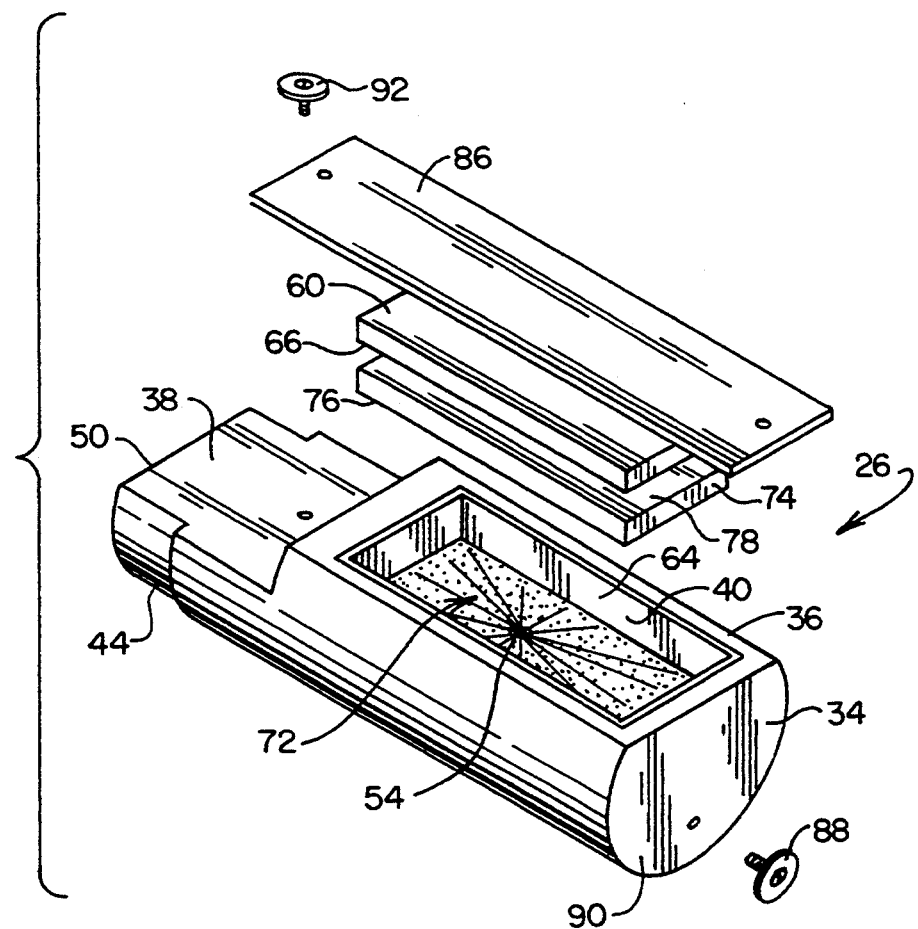
FIG. 5 is an exploded perspective view of a crystal and associated crystal mount employed with the instrument of FIG. 1.

Looking to FIGS. 4 and 5, the structuring of the crystal mounting arrangement 26 is revealed at an enhanced level of detail. In the figure, a crystal mount 34 which is formed of a material selected to attenuate gamma radiation such as lead is provided which is inserted within the passageway of rod 14 at the detector support portion 18. This mount 34 is seen to be generally cylindrical in shape with a flattened or truncated upwardly disposed surface 36 and a stepped down surface portion 38. Formed inwardly from the flat surface 36 is a rectangular crystal receiving and supporting cavity 40. The mount 34 is seen to be positioned within a separate or discrete cylindrical tip component 42 of the tube 14. In this regard, the component 42 is seen to be flattened to define the window surface 22 and is slidably mounted over a stepped down surface 44 (FIG. 4) turned within tube 14. Retention of this tip component 42 upon the stepped down surface 44, for example, is provided using an electrically conductive epoxy cement. In this regard, the connection must be such as to assure no leakage of body fluids within the passageway 46 formed within tube 14. Note that the upwardly disposed fiat surface 36 of the mount 34 is spaced in close adjacency with the underside of the window component 22 of tip component 42. This permits the positioning of a radiation responsive crystal as close as possible to that surface window 22. FIG. 4 shows an opening or conduit 48 formed within the mount 34 which extends from an opening 50 within the rearward surface of mount 34 to a corresponding opening 54 at the bottom surface of cavity 40.

Figure 6:
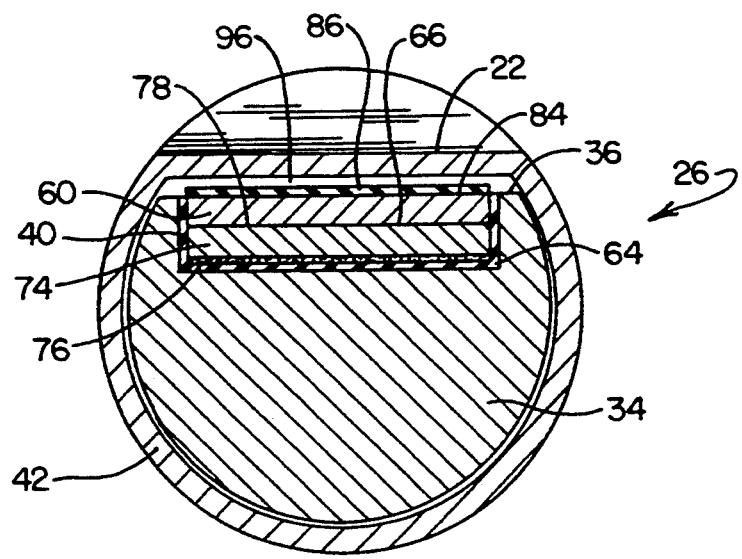
FIG. 6 is a sectional view taken through the plane 6—6 shown in FIG. 4.

The configuration thus depicted in connection with FIGS. 4–6 is one intended for use in detecting locators labeled with gamma emitting radiation, and, particularly, emitted from $^{125}$I which, for the surgical performance contemplated will be of very low energy level. Cadmium-zinc-telluride detecting crystals are employed for this purpose. Such crystals are marketed by Aurora Technologies, Inc., San Diego, Calif. For the present laparoscopic instrument, it is desirable that the crystal used for detection have as large a surface area as is practical to improve counting efficiency. Preferably, that active surface area will be equivalent to the surface area of forward looking crystal mounts as are used in conventional RIGS surgery. To achieve this requisite active surface area while maintaining necessarily restricted instrument diameters, a rectangular cadmium-zinc-telluride crystal 60 is employed having a principal lengthwise dimension in parallel with the central axis 62 of the tube 14. Because cadmium telluride crystals exhibit microphonic (piezoelectric) effects, their mounting for the instant use requires a rigid avoidance of noise generated by rubbing or by the transmission of acoustical noise or the like into the crystal 60 from its mounting environment. To achieve this requisite mounting with an avoidance of microphonic induced noise, the cavity 40 is initially covered with an electrically insulative polymeric layer 64. Preferably, the layer 64 is formed of silicone, generally referred to as silicone rubber which is an elastomer in which the C linkages of a polymerized hydrocarbon are replaced by Si—O linkages. It is sold, for example, under the trademark "SILASTIC". In this regard, the layer 64 can be developed as a rectangular receptacle with a rectangular mold carrying a conventional mold release. A necessary electrical bias, for example at 60 v, is asserted at the rearward surface 66 of the crystal 60 by an electrical contact arrangement including multi-strand wire 68 seen extending from connection with a circuit board 70 in FIG. 4 and through the opening 50 of passageway 48 to opening 54 within the cavity 40. From this opening 54, the plurality of strands of this wire are "spread out" over the polymeric layer 64 as seen in general at 72 in FIG. 5. Additionally, positioned over the electrically insulative polymeric layer 64 at the bottom of the cavity 40 is an electrically conductive cushion layer 74 having a lower disposed surface 76 positioned over the strands 72 and upon the forwardly facing surface of layer 64. To avoid microphonically induced noise, this lower disposed surface 76 of the cushion layer 74 is adhered to the upper surface of the heat-stable silicone robber. Additional amounts of the "SILASTIC" material may be used for this purpose. Advantageously, the electrically insulative elastomeric adhesive retains its elastic properties over time and high temperature conditions. With the arrangement thus shown, electrical bias, as well as electrical communication with respect to charge transfer is asserted from the contact strands 72 into this electrically conductive cushion layer to its upwardly disposed surface 78. Preferably, the electrically conductive cushion layer 74 is provided as a non-woven TEFLON cloth which is carbon filled to the extent rendering it an effective conductor of electricity. In general, the material is a carbon containing stretched, highly crystalline, unsintered polytetrafluoroethylene marketed under the trademark "Gore-Tex".

The lower or rearward surface 66 of the cadmium-zinc-telluride crystal 60 is freely abuttably positioned over the upwardly disposed surface 78 of electrically conductive cushion layer 74. No adhesive is employed in this union other than some of the silicone adhesive may migrate about the edge of the crystal 60 with beneficial effect. This positions the upwardly disposed surface of crystal 60 as at 84 in close adjacency with the underside of the window 22. To retain the assemblage of crystal 60 and associated mount in position, a thin elastomerically deformable sheet 86 is stretched over the assembly including the upwardly disposed surface 84 of crystal 60. This compressibly urges the crystal downwardly to improve device performance. The thin sheet 86 may be provided as a carbon-filled rubber and thus serves the second purpose of asserting necessary ground at the surface 84 of crystal 60. Note in this regard, that in stretching the sheet 86 over the crystal 60, it is fastened by machine screw and washer combination 88 at the forward or tip portion 90 of mount 34 seen in FIG. 4. The opposite end of the sheet 86 is similarly fastened to surface 38 of mount 34 by a machine screw and washer arrangement shown at 92 in FIGS. 4 and 5. Ground is conveyed to the sheet 86 from the lead mount 34 which, in turn, is coupled to ground through the forward stage 28 of the preamplifier function. Note that the circuit board 70 is seen attached to surface 38 of mount 34 with a screw 94.

Thus mounted within the detector support region 18 of instrument 10, the upwardly disposed surface 84 of crystal 60 is spaced from the underside of window 22 by a very small gap 96 to avoid acoustic or vibrationally induced noise. However, the distance from the outwardly disposed surface of window 22 to that upwardly disposed surface of crystal 60 is quite small, being, for example, less than 2 mm. This permits the upwardly disposed surface 84 of crystal 60 to be positioned in very close proximity to the tissue under investigation. It is the flatness of the window 22 within the generally cylindrical instrument 10 which additionally permits this close positioning of the crystal to the tissue under investigation. Such distancing for the purpose of the operation of instrument 10 is quite important in view of the low level of radiation involved and the noted approximate inverse square relationship of radiation propagation with which the system performs.

Figure 7A:
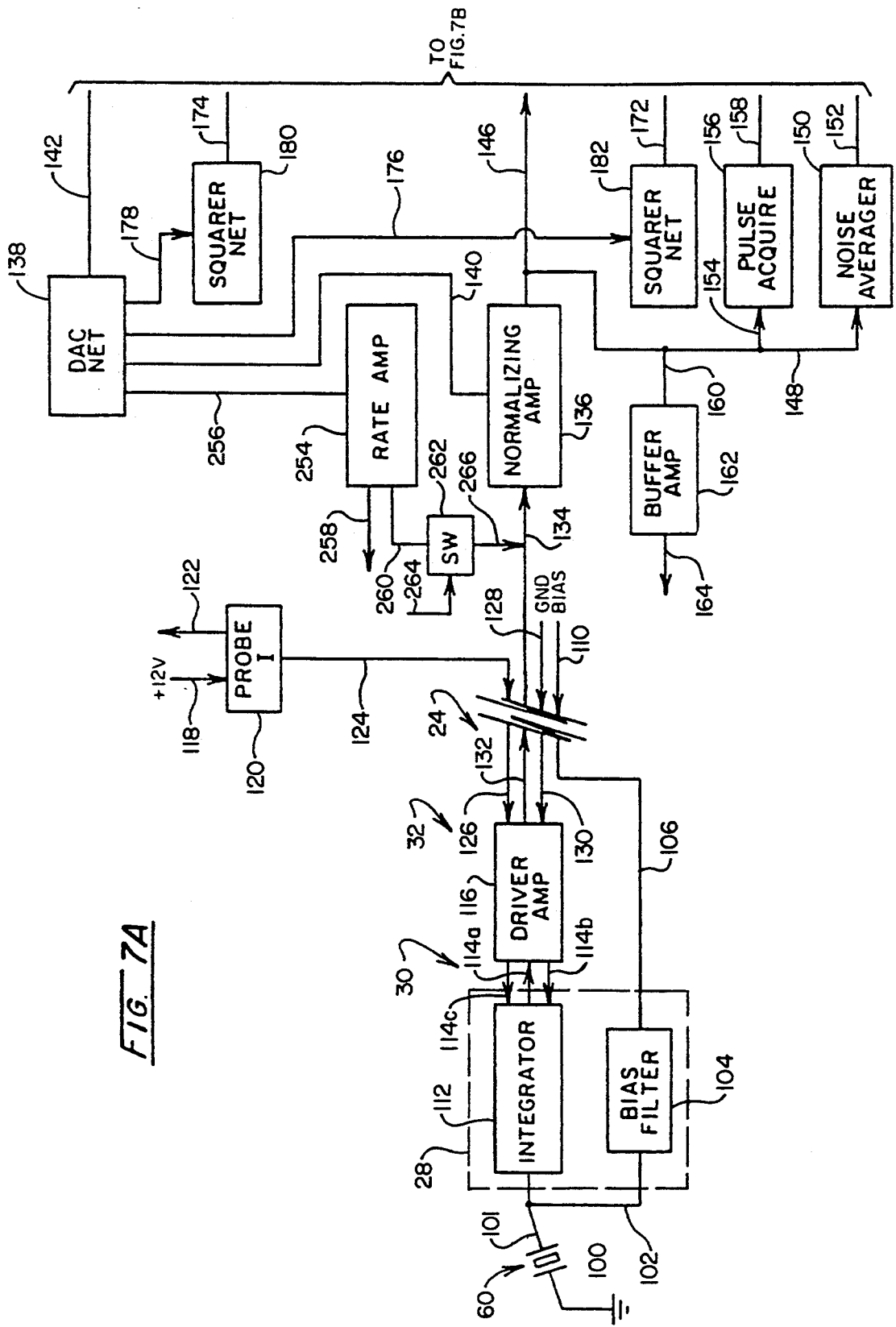
FIGS. 7A and 7B combine as labeled to form a block diagram of the functional components of a signal treatment and control system associated with the instrument of the invention.
Figure 7B:
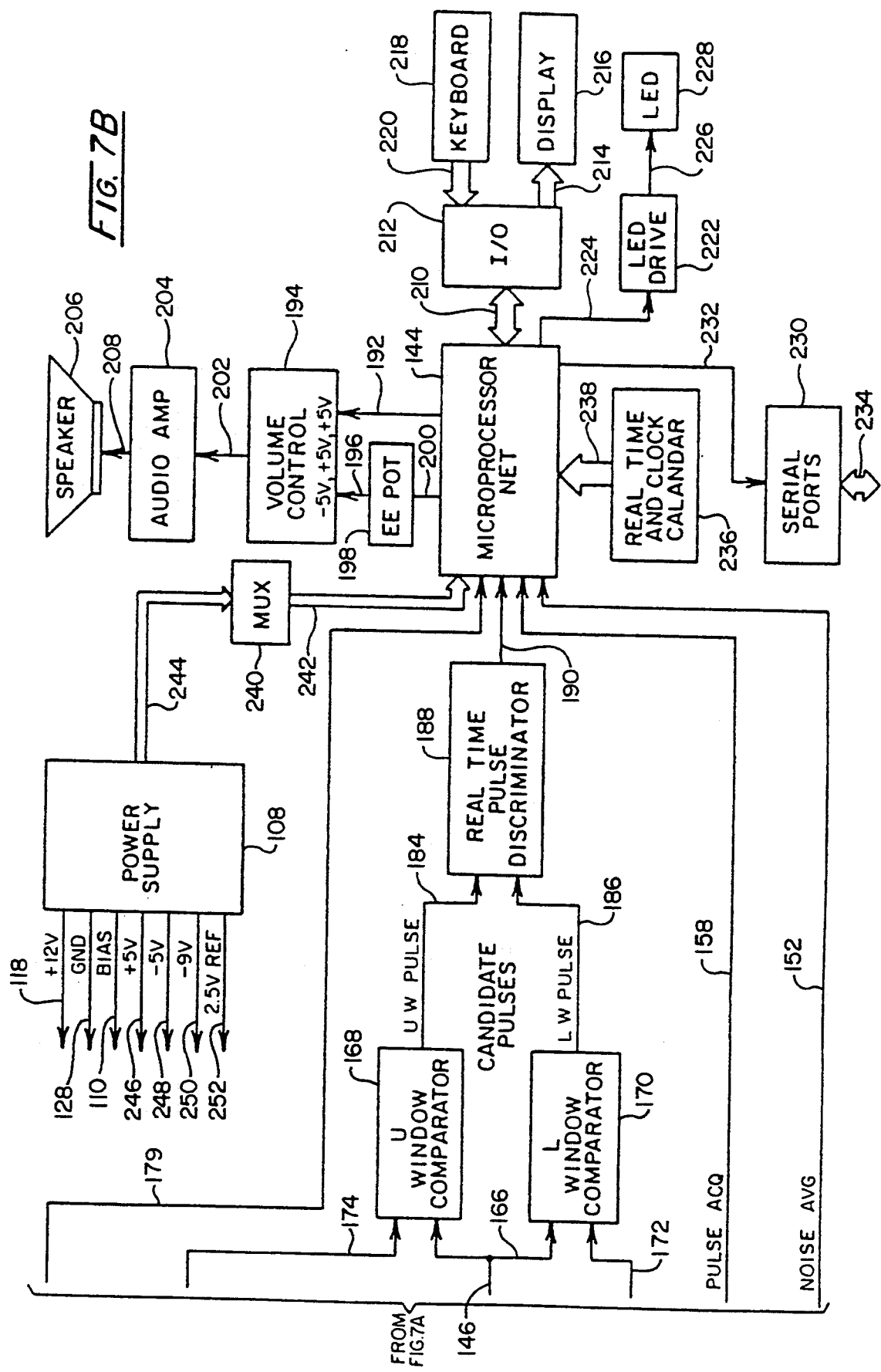

Referring to FIGS. 7A and 7B, a block diagrammatic representation of the signal treatment and control circuitry employed with instrument 10 is revealed. In FIG. 7A, that crystal which is being employed, for example crystal 60 as labelled, is shown having one face coupled to ground through line 100, while the opposite, biased face thereof is coupled via lines 101 and 102 to a bias filter represented at block 104. Bias Filter 104 is part of the earlier-described forward preamplification stage 28 herein identified in FIG. 7A by a dashed boundary with the same numeration. The input to the filter 104 is derived ultimately from cable 24 (FIG. 1) and is represented in FIG. 7A at line 106 as being applied through that cable again represented by numeral 24. Line 101 corresponds with line 68 earlier described in connection with FIG. 4 and supplies an appropriate bias, for example, 60 v to the rearward surface of crystal 60. This bias emanates from a power supply shown at block 108 in FIG. 7B and represented at line 110.

Line 101 from crystal 60 is shown extending to an integrator stage 112 of the first preamplification stage 28. The integrated valuation of a detected radiation disturbance or charge categorized signal then is shown directed as represented by line 114a to a driver-amplification network shown at block 116. Line 114a additionally is a part of the shielded cable 30 extending through the passageway 46 of access tube 14 to the second preamplification stage 32 within base 12 as described in connection with FIG. 3. Cable 30 also may carry gound and +12 v supply as shown, respectively, at lines 114b and 114c. The noted 12 v power supply as represented at line 114c is derived for the driver amplifier stage 116 from the power supply 108 (FIG. 7B) as represented at line 118 which, as shown in FIG. 7A, is directed to a probe current network represented by block 120. Under microcomputer control as represented by line 122, the network 120 develops signals, for example, determining whether the probe instrument 10 has been properly connected to console based control system (now shown) described in detail in U.S. Pat. No. 4,801,803 incorporated herein by reference. Delivery of the 12 v power supply for the preamplifier stage 32 is represented at line 124 as extending to the driver-amplifier 116 via cable 24 and line 126.

Ground to the instrument 10 also is developed from the power supply block 108 as represented at line 128 shown in FIG. 7A as extending to cable 24 and via line 130 to the driver-amplification stage 116.

The output of the driver-amplification surge 116 is represented at line 132 extending through the cable 24 and then being represented as line 134 to the input of a normalizing amplifier represented at block 136. The network represented by block 136 functions to amplify or attenuate, i.e. scale the noise characteristic of any given instrument 10 and normalize the value thereof or render it consistent for letter comparison stages. Generally, for example, the 27 kev energy level gamma ray generated pulses in a system employing $^{125}$I will be about five times higher than noise levels. Normalizing amplifier network 136 will establish those noise levels at some predetermined level, for example, 200 millivolts, and the resultant proportional valid gamma related pulses will become about 1 v high for purposes of ensuing comparison functions. It may be observed that the amplifier network at block 136 is controlled from a digital-to-analog converter network represented at block 138 via line 140. Network 138, in turn, is controlled from line 142 extending, as shown in FIG. 7B, to block 144 representing a microcomputer network. The normalized output developed from network 136 is presented along lines 146 and 148 to a noise averager circuit as represented at block 150. This network 150 determines an average amplitude, value for the noise of a given system with a given instrument 10 and provides corresponding signal as represented at line 152 (noise avg) which is employed as above described as information used by the microcomputer 144. This information, in addition to being employed with the normalizing amplifier network represented at block 136, may be used to develop a low window valuation for the comparison function.

Line 148 also extends via line 154 to a pulse acquire network represented at block 156. This network functions, when activated, by the microcomputer represented at block 144, to acquire the value of the highest pulse amplitude witnessed at line 154. Periodically, this information then is transmitted to the microcomputer at block 144 as represented by line 158 (Pulse Amp.). Representing a form of peak detector, the network is sometimes referred to as a "snapshot circuit". Also produced from lien 148, as at line 160 and block 162, is a buffer amplifier which will provide at line 164 an output representing received pulses which may be made available to the system, for example, at a console (not shown).

Line 146 extends, as shown at FIG. 7B, at line 166, to one input of an upper window comparator represented at block 168 and a lower window comparator illustrated at block 170. The threshold level for comparative purposes employed by the network at block 170 is shown asserted from line 172 and, preferably, is developed by the logic of microcomputer network 152. Of course, manual setting of such windows can be carried out. In similar fashion, the upper window of acceptance for valid radiation interaction is established from a corresponding line 174. This threshold setting may be made from the information taken from pulse acquire network 156.

Returning to FIG. 7A, the upper window and lower window threshold selections are made under the control of the microcomputer network at block 144 which controls the digital-to-analog network shown at block 138. It is the characteristic of such networks as at block 138 to provide an output which is comprised, for example, of 256 steps of varying amplitude. The percentage of incrementation from step to step will vary somewhat over a range of voltage values provided. Accordingly, the outputs from this conversion network at block 138, as shown at lines 176 and 178 are directed to squarer networks shown, respectively, at blocks 180 and 182. These networks function to square the current outputs at lines 176 and 178 and thus achieve a uniform percentage incrementation of the threshold defining outputs at lines 172 and 174.

Returning to FIG. 7B, the outputs of the comparator networks shown at blocks 178 and 170 represent candidate pulses which may be above or below the given thresholds and are identified as being presented as "UW pulse" and "LW pulse" along respective lines 184 and 186. These lines are shown directed to a real time pulse discriminator network represented at block 188 which carries out Boolean logic to determine the presence or absence of valid pulses. Valid pulses are introduced to the microcomputer network 144 as represented by line 190.

The microcomputer network represented at block 144 performs under a number of operational modes to provide both audio and visual outputs to aid the surgeon in locating and differentiating tumorous tissue. In the former regard, as represented at line 192 and block 194, a volume control function may be asserted with amplitude variations controlled from a solid-state form of potentiometer represented at line 196 and block 198. Control to potentiometer 196 is represented at line 202 to an audio amplification circuit represented at block 204 for driving a speaker as represented at 206 and line 208. With the noted siren arrangement, the frequency output from speaker 206 increases as the instrument 10 is moved closer to the situs of concentrated radiation. Of course, conventional clicks and beeps can be provided at the option of the operator.

The microcomputer network 144, as represented by bus defining arrow 210 and block 212 also addresses an input-output network which, as represented at bus arrow 214, functions to provide a pulse count output of varying types as well as outputs representing volume levels, pulse height, noise levels, and battery status. These outputs are provided in visual formal at a visual display represented at block 216. Similarly, the input-output function represented at block 212 provides appropriate scanning of switches or the like may be employed with the control system and are represented by block 218 and bus input arrow 220. During a given counting operation, the microcomputer network at block 144 functions to control a light emitting dime drive network represented by block 222 from line 224. The drive network represented at block 222 is shown providing an input, as represented by line 226, to a light emitting diode (LED) display as represented by block 228. A serial output port of conventional variety also may be provided with the system, such ports being represented at block 230 being addressed from the microcomputer represented at block 144 from line 232 and having output and input components represented by arrow 234. A real time clock-calendar having a nonvolatile memory also may be provided in conjunction with the functions of the microcomputer network 144 as represented by block 236 and bus arrow 238. Further, the microcomputer may be employed to monitor the performance of the power supply represented at block 108. This is shown being carried out by the interaction of the microcomputer network with a multiplexer represented at block 240 and having an association represented by arrows 242 and 244. It may be observed that the power supply also provides a +5 v source for the logic level components of the circuit as represented by lien 246; a −5 v source at line 248, as well as a −9 v source at line 250 for purposes of display drive, and finally, a 2.5 v reference as represented at line 252 to provide reference input for the preamplification analog circuitry.

Returning to FIG. 7A, the microcomputer network as represented at block 144 also provides an input to the digital-to-analog conversion network represented at block 138 which corresponds with the instantaneous pulse rate and this information is conveyed to a pulse rate amplifier network represented at block 254 via line 256. The resultant output, as represented at line 258, may be provided, for example, at a convenient location upon a console. This circuit represented at block 254 also may be employed to generate a calibrating pulse for testing the downstream components of the system. Thus, the microcomputer represented at block 184 applies a predetermined pulse level through the digital-to-analog conversion network at block 138 for presentation to the amplifier network represented at block 254. The resultant output at line 260 is selectively switched, as represented by block 262, to define pulse width from the microcomputer input at line 264 to the calibrating pulse at line 266.

The method of the invention employs the instrument 10 and its associated control circuitry in a diagnostic manner wherein the advantageous aspects of laparoscopic procedures are utilized to determine a subsequent treatment modality. In this regard, where primary tumor is indicated which has not metastisized, then a laparoscopic-based resection is called for as the treatment modality. Under such a diagnosis, the patient then is surgically treated laparoscopically with the avoidance of a substantial trauma of open surgery. On the other hand, where a radionuclide survey of lymph regions carded out with instrument 10 indicates that lymph node or metastatic disease involvement is present, then open surgical treatment is indicated. Colorectal cancer may spread by local invasion, lymphatic extension, hematogenous spread, or implantation. After the initial mucosal growth, a tumor may progress locally in several directions, but usually it protrudes first, as noted above, into the lumen. Mural penetration may result in local failure or peritoneal seeding.

Colorectal cancer first metastasizes to the perirectal nodes at the level of the primary tumor or immediately above it. Next, the chain accompanying the superior hemorrhoidal vessels is involved. In later stages of disease, when the hemorrhoidal lymphatics are blocked, there is lateral or downward spread. In colon carcinoma, normal lymphatic flow is through the lymphatic channels along the major arteries, with three echelons of lymph nodes: pericolic, intermediate, and principal. If tumors lie between two major vascular pedicles, lymphatic flow may drain in either or both directions. If the central lymph nodes are blocked by tumor, lymphatic flow can become retrograde along the marginal arcades proximally and distally. The risk for lymph node metastases increases with increasing tumor grade, as does the number of lymph nodes affected.

The liver is the primary site of hematogenous metastases, followed by the lung. Involvement of other sites in the absence of liver or lung involvement is rare.

Implantation refers to the release of tumor cells from the primary tumor and their deposition on another surface. Implantation has been reported with tumor cells shed intraluminally, from the serosal surface through the peritoneum, and by surgical manipulation and resultant deposition on wound surfaces.

See generally:

"Second-Look Surgery for Colorectal Cancer, The Second Time Around" by Martin, et al., Ann. Surg. Vol. 214, No. 3, pp 321–327, September 1991.

"Manual for Staging Cancer" Fourth Ed. Edited by Beahrs, et al., pp. 75–82, 1992, J. B. Lippincott Co., Philadelphia. Pa.

The method also looks to recurrent tumor wherein a patient presents the signs of recurrency, for example, through rising CEA levels or from a CAT scan or colonoscopy, then the procedure employs laparoscopic radionuclide survey to determine whether a metastisized condition is at hand and the extent of such metastisis. In the event that the cancer is determined to be too extensive and is thus inoperable, no further surgical procedure other than the removal of blocking lesions is indicted, open laparotomy is not resorted to and the trauma associated with an open and close open surgical procedure is avoided with minimized patient trauma.

The method is commenced with conventional RIGS surgical procedure wherein an effective amount of radiolabeled locator which specifically binds a marker produced by or associated with neoplastic tissue is administered to the patient. Typically, a monoclonal antibody (MAb) coupled with a radiolabel such as $^{125}I$ is utilized. Next, the radiolabeled locator is permitted to preferentially concentrate at any of such markers to an extent increasing the ratio of photon emissions from the marker to background photon emissions in the patient. Then, following more conventional laparoscopic procedure, the peritoneal cavity of the patient is insufflated and access to the insufflated cavity is made through a plurality of cavity access cannulas. In general, a trochar is associated with the cannulas which provides the opening through the abdominal wall.

Figure 8:
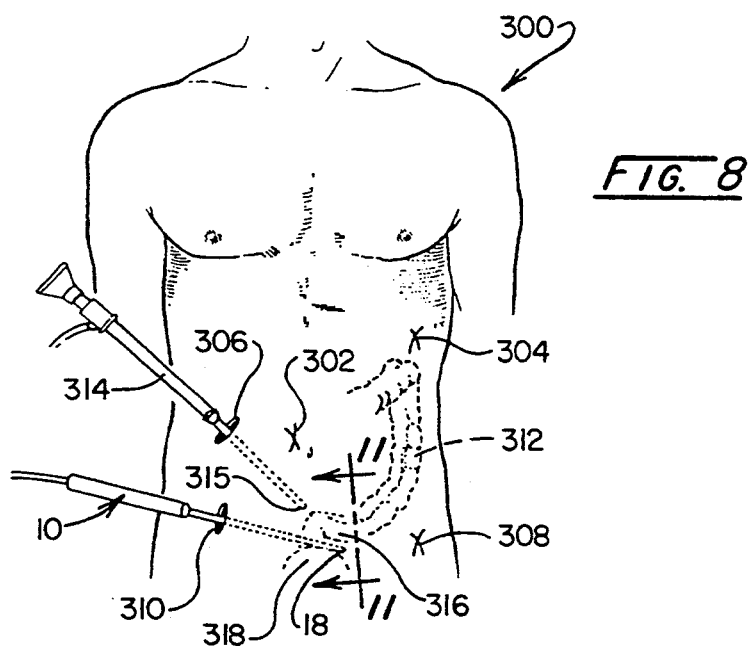
FIG. 8 is a partial frontal view of a patient showing portions of the colon in phantom, the location of access openings for laparoscopy and instrumentation employed with the invention.

Looking to FIG. 8, cannula positions as may be employed with the instant procedure are represented in connection with the schematic representation of a patient 300. In general, one opening as at 302 will be provided near the umbilicus. Portals then may be placed at the left upper quadrant as represented by an X at 304; at the fight upper quadrant its represented symbolically at 306; at the left lower quadrant as represented by an X at 308; and at the fight lower quadrant as represented symbolically at 310. Shown inserted through a cannula at 310 is the instrument 10, the detector portion 18 of which is represented as being located to carry out a portion of a radionuclide survey in the region between the bladder and sigmoid colon of patient 300. In the figure, the descending colon is represented in phantom at 312; the sigmoid colon at 316 and the bladder at 318.

Shown inserted through a cannula at portal 306 is a laparoscope 314 having an illuminating and visualizing tip 315 which is pointed toward the region of survey by detector support portion 18 of instrument 10. Generally, the imaging carried out by the instrument 314 will be observed by the surgeon ,and assistants at a high definition television screen adjacent the operating theater.

In accordance with the diagnostic procedure at hand, the real time camera represented by instrument 314 initially is utilized to survey the colon for the purpose of detecting any visual indication of neoplastic tissue. Particularly where primary tumor is hand, that visual survey usually will not locate tumor, inasmuch as the growth of such tumor is intraluminal, i.e. commences within the interior structure of the colon. Thus, a visual survey of the colon typically will not identify tumor.

Figure 9:
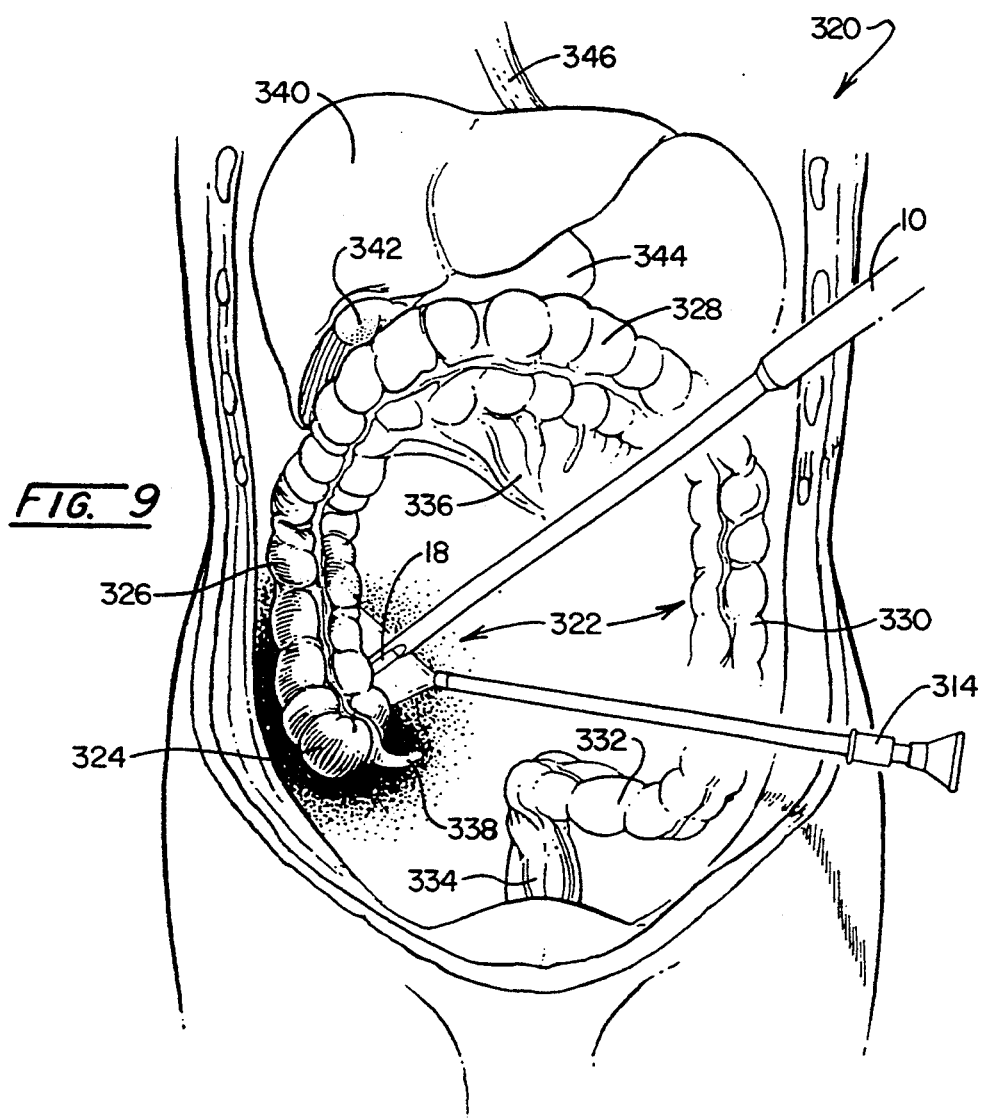
FIG. 9 is a sagital partial view of a patient showing portions of the colon and adjacent organs in conjunction with a positioning of instrumentation employed with the invention.

Looking to FIG. 9, a sagital section of a patient 320 is illustrated showing instrument 10 under the visualization of laparoscope 314 in the course of carrying out a radionuclide survey of the colon represented generally at 322. Colon 322 includes the caecum 324, the ascending colon 326, the transverse colon 328, the descending colon 330, the sigmoid colon 332, and the rectum 334. Transverse colon 328 is seen in an upwardly retracted orientation improving its accessibility and a portion of the mesentery 336 is shown extending from the transverse colon. Below the caecum 324 is an appendix 338. The retracted transverse colon 328 is seen extending in an upwardly directed arc toward the liver 340 which is see to extend over a gallbladder as at 342 and pancreas 344. A portion of the esophagus is seen extending upwardly at 346. Not seen in FIG. 9 is the small intestine as well as the greater omentum, the former generally filling the space outlined by colon 322 and the latter appearing somewhat like a curtain of tissue which overlays the organs within the peritoneal cavity.

Figure 10:
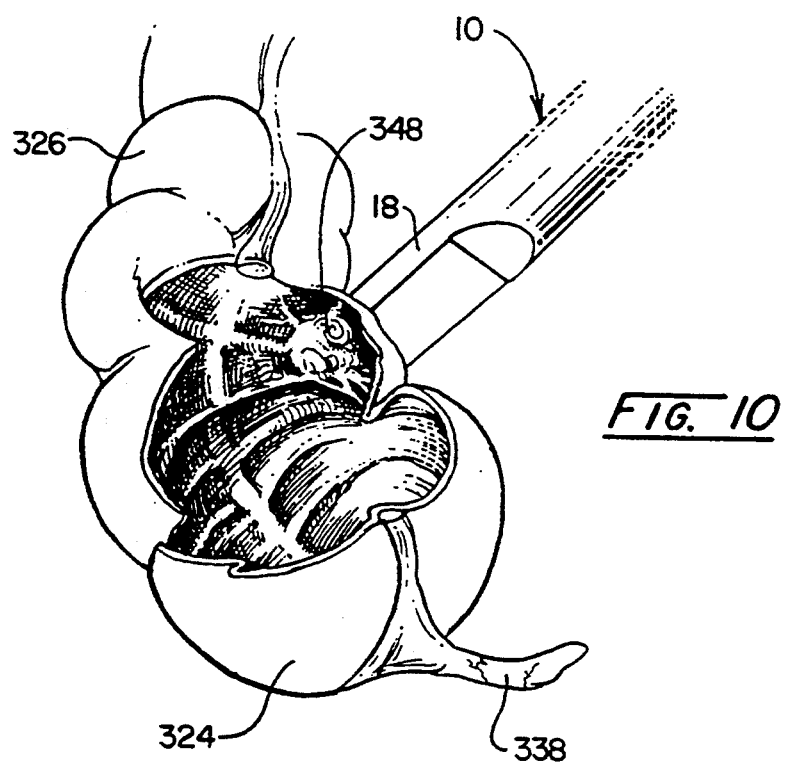
FIG. 10 is a perspective view of a portion of the ascending colon shown in FIG. 9 with portions broken away to reveal internal tumor.

For a condition of primary tumor of sufficiently early development, a visual survey of the colon 322 with instrument 314 will reveal no neoplastic tissue, inasmuch as such tumor commences growth within the lumen of the colon and only becomes observable at the outside wall of the colon when it has matured somewhat. However, with the radiolabeled locator approach of the present method, following a visual survey of colon 322 with instrument 314, then a radionuclide survey of colon 322 is carried out with instrument 10. The latter survey is carried out under observation from instrument 314 to the extent possible. Instrument 314 is seen in the present illustration as being inserted through a cannula located at the left lower quadrant, while instrument 10 has been inserted through a cannula located in the left upper quadrant. Detector support portion 18 of instrument 10 is seen being maneuvered in adjacency with colon 322, for the present demonstration being located at the lower end of the ascending colon 326. Looking additionally to FIG. 10, the arrangement of instrument 10 and the lower portion of ascending colon 326 are reproduced, showing in broken away fashion, a pre-emergent tumor 348 which cannot be visualized at the outer surface of ascending colon 326. However, because of the adjacency of detector portion 18 of instrument 10 with the radiolabeled locator detected tumor 348, the surgeon will be given an immediate audible indication of the presence of tumor 348. By further surveying along the colon 322, a demarcation of the range of tumor involvement can be made under the visualization of instrument 10 by instrument 314. Following an identification of tumor 348, the procedure then provides for carrying out a radionuclide survey of lymph nodes within the peritoneal cavity. Initially, the survey will take place in the vicinity of the located tumor 348. Lymph nodes being located, for example within the mesentery and elsewhere. Additionally, the radionuclide survey will identify any other metastatic disease at which locator will have concentrated.

Figure 11:
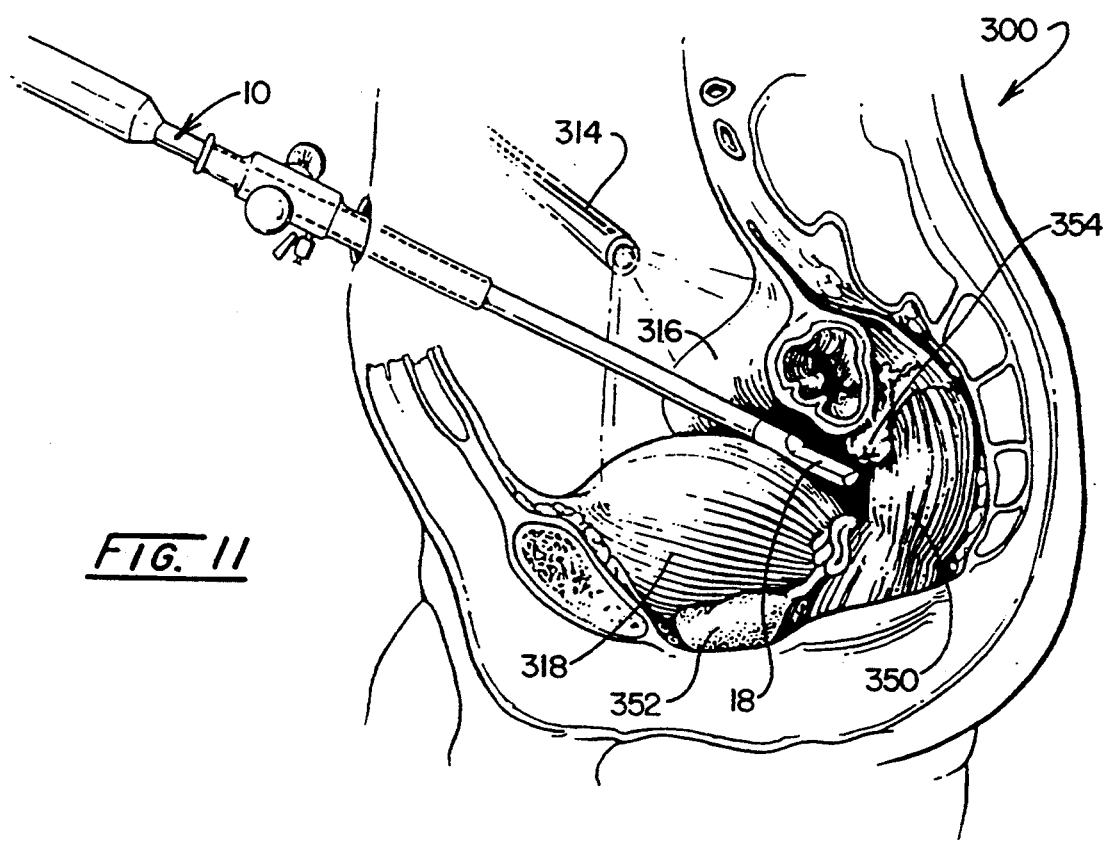
FIG. 11 is a partial anatomical view of the patient of FIG. 8 taken through the section 11—11 therein.

Because of the various earlier-described regions of organs encountered by the surgeon in the survey both of the colon 322 and lymph or other metastatic disease organ involvement, visualization will not always be available through instrument 314. Returning to FIG. 8, non-visualizing aspect of the preliminary survey of the colon is illustrated. In this regard, the instrument 10 will have been employed to carry out a radionuclide survey of the colon including the descending colon 312. However, as this survey moves lower into the abdomen, for example, as shown in the region between the sigmoid colon 316 and bladder 318, the detector support portion 18 of instrument 10 will not be visualizable by instrument 314. Looking to FIG. 11, a more detailed representation of this component the radionuclide survey is revealed. In the figure, the sigmoid colon 316 again is illustrated as it is adjacent to the rectum 350, bladder 318, and prostate gland 352. During this portion of the radionuclide survey, the detector support portion 18 of instrument 10 will have moved into adjacency, for example, with a hidden tumor 354 located at the underside of sigmoid colon 316. Not seen in FIG. 11 are other organs such as the small intestine, the omentum, and the like.

For the form of cancer involvement, for example as represented at tumor 354, the treatment modality indicated by the invention calls for an open laparotomy in view of the inaccessible location of tumor 354 with respect to a laparoscopic-based procedure. The procedure of the present invention also calls for that open laparotomy indication wherever the survey carried out with instrument 10 shows lymph node involvement or other metastatic disease.

Figure 12:
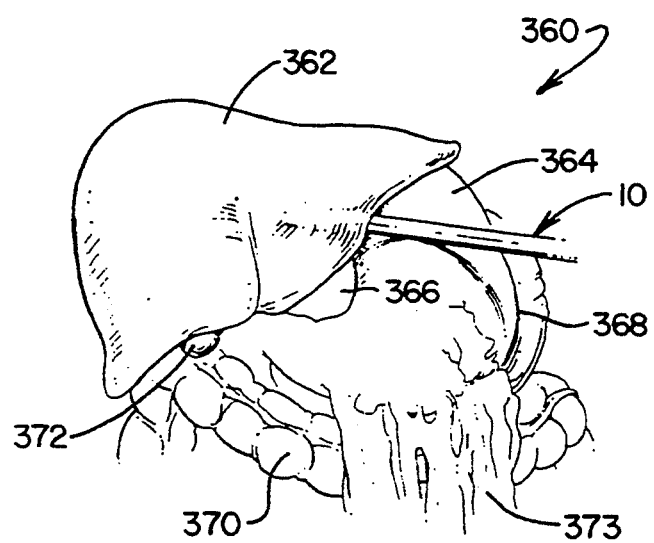
FIG. 12 is a perspective view of a transverse colon, stomach and liver showing the positioning of an instrument according to the invention.

The deeper regions of the anatomy explored during the radionuclide survey for lymph node involvement as well as other metastatic disease additionally looks above the transverse colon and beneath the liver in the region of the gastrohepatic ligament. Looking to FIG. 12, that region is represented at 360, the figure revealing the liver 362 in its more normal orientation; the stomach 364 with lesser curvature 366 and greater curvature 368 located above the transverse colon 370. A portion of the gallbladder is seen at 372 and portion of the greater omentum is shown at 373 draping over the transverse colon 370. Instrument 10 is seen in a process of being use to carry out a radionuclide survey of the region beneath the liver 362, the device positioning the detector end beneath the left lobe of the liver 362. The gastrohepatic ligament generally is located above the lesser curvature 366 of stomach 364, for example, at 374.

Should lymph node involvement or other metastatic disease be determined to be present by this radionuclide survey, then a determination of treatment modality indicates a procedure wherein open laparotomy is carried out as representing the most beneficial treatment morality. The region 360 being explored is involved with highly significant organs such that an error in laparoscopic procedure may lead to highly undesirable results, for example, the damaging of a vein or artery.

Figure 13:
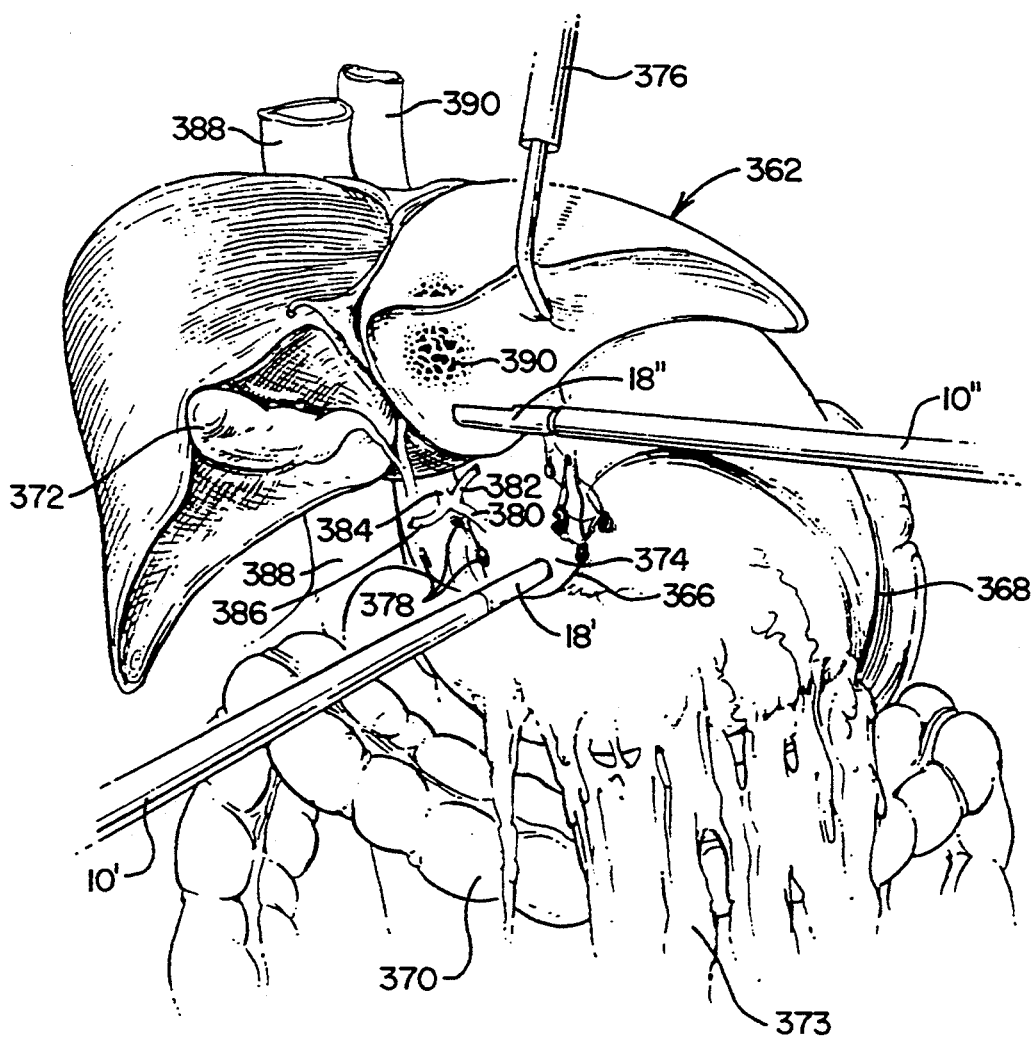
FIG. 13 is an enlarged view of the subject of FIG. 12 showing a retraction of the liver and the alternate positioning of instruments according to the invention.

Typically, the surgeon, upon being apprised by the radionuclide survey that lymph node involvement or other metastatic disease is present, will look further prior to terminating the laparoscopic procedure. For example, in FIG. 13, the liver 362 is shown retracted by a procedure including the use of retracting instruments such as that shown at 376. This reveals the gastrohepatic ligament 374. Surveyed at the ligament 374 by, for example, the instrument 10, now identified at 10', are celiac nodes 378 which are shown in juxtaposition, with the splenic artery 380; the left gastric artery 382: the celiac trunk 384; and the common hepatic artery 386. The delicacy of this survey is further brought to light by the proximation at this region of the inferior vena cava 388 and the abdominal aorta 390. As is apparent, a location of lymph node involvement at the gastrohepatic ligament 374 will result in a determination that the appropriate treatment modality indicates that an open laparotomy is called for. FIG. 13 also reveals an identification of an embedded and non-visual tumor shown in phantom at 390 within the interior of the left lobe of liver 362. This metastatic disease involvement will be located, for example, by the radiation responsive instrument 10 as positionally represented at 10″ as its detector support portion here represented at 18″ is brought into proximity with the region of the underside of the liver 362 which is in the path of radiation emanating from the locator concentrated at the neoplastic region 390.

Summarizing the method for determining the treatment modality for neoplastic tissue as discussed above, the following steps may be observed:

the patient is administered an effective amount of a radiolabeled locator which specifically binds a marker produced by or associated with neoplastic tissue;

the radiolabeled locator is permitted to preferentially concentrate at any marker to an extent increasing the ratio of photon emissions from the marker to background photon emissions in the patient;

after the concentration of locator, the peritoneal cavity of the patient is insufflated and access thereto is provided through a plurality of cavity access cannulas;

a real time laparoscopic camera arrangement is provided with the display for visualization of select regions of the cavity by access to one or more of the cannulas;

a laparoscopic radiation detection system as described is provided;

the colon is visually surveyed within the cavity by accessing the camera arrangement thereto through a select one or more of the access cannulas and a determination is made as to whether any visual indication of neoplastic tissue is present;

there is then carried out a radionuclide survey of the colon within the cavity by manipulating the elongate accessing tube of the radiation detection system through one or more of the access cannulas to maneuver the window thereof along and in substantial adjacency with the colon under visualization at the camera display to the extent such visualization is possible, to detect and differentiate tissue at which the locator has concentrated by correlation of the perceptible output signals of the system to the position of the window with respect to the colon;

the radionuclide survey of the lymph nodes within the cavities then is carried out by manipulating the elongate accessing tube of the radiation detection system through one or me of the cannulas to maneuver the window into substantial adjacency with the lymph nodes to detect and locate a lymph node or other metastatic disease at which the locator is concentrated by correlation of the perceptible output signals of the system to the position of the window as visualized from the camera arrangement display; and then a determination of the treatment modality is made based upon the visual survey of the colon and by the radionuclide surveys of the colon and lymph nodes.

Where the patient is diagnosed prior to the surveys as presenting neoplastic tissue as primary tumor and the step for visually surveying the colon is carried out with the absence of any visual indication of neoplastic tissue; the radionuclide survey of the colon locates and differentiates tissue at which locator has concentrated; and the step for carrying out the radionuclide survey of the lymph nodes locates no lymph node or metastatic disease at which locator has been concentrated, then the determination of treatment modality indicates that a laparoscopically assisted removal of the located and differentiated neoplastic tissue is beneficial as a treatment modality. Under these conditions, the patient essentially is treatable at minimum trauma utilizing minimally invasive laparoscopic surgery.

Where the patient is diagnosed prior to the surveys as presenting neoplastic tissue as primary tumor; and the step of visually surveying the colon is carded out in the absence of a visual indication of neoplastic tissue; and the step for carrying out a radionuclide survey of the colon locates and differentiates tissue at which locator is concentrated; and the step for carrying out a radionuclide survey of the lymph nodes locates a lymph node at which locator has concentrated, then the determination of a treatment modality indicates that the carrying out of an open laparotomy to remove the located and differentiated neoplastic tissue is beneficial as a treatment modality.

Where the patient is diagnosed prior to the surveys as presenting neoplastic tissue as primary tumor; and the visual surveying of the colon is carded out with the result of a presence of a visual indication of neoplastic tissue; and the radionuclide survey of the colon differentiates the tissue at which the locator is concentrated; and the step for carrying out radionuclide survey of the lymph node locates no lymph node or metastatic disease at which the locator is concentrated; then the determination of treatment modality indicates that carrying out a laparoscopically assisted removal of the located neoplastic tissue is beneficial as a treatment modality.

Where the patient is diagnosed prior to the surveys as presenting the neoplastic tissue as recurrent tumor; and the radionuclide survey of lymph nodes locates a lymph node or other metastatic disease at which locator has concentrated: then the determination of treatment modality indicates a procedure employing surgical resection would not be beneficial to the patient. For this condition, the patient is spared the trauma associated with an open laparotomy which would represent an "open and close" procedure with perhaps only minor resection of blocking lesions or no further treatment.

Since certain changes may be made in the above-described method without departing from the scope of the invention herein involved, it is intended that all matter contained in the description thereof or shown in the accompanying drawings shall be interpreted as illustrative and not in a limiting sense.

We claim:

1. A method for determining a treatment modality for neoplastic tissue within the peritoneal cavity of a patient, comprising the steps of:

administering to said patient an effective amount of radiolabelled locator which specifically binds a marker produced by or associated with neoplastic tissue;

permitting said radiolabelled locator to preferentially concentrate at any said marker to an extent increasing a ratio of photon emissions from said marker to background photon emissions in said patient;

after said concentration, insufflating said peritoneal cavity and providing access thereto through a plurality of cavity access cannulas;

providing a real time laparoscopic camera arrangement with a display for visualization of select regions of said cavity by access through one of said cannulas;

providing a laparoscopic radiation detection system including:
- a base portion engageable by a surgeon,
- an elongate accessing tube fixed to said base portion, dimensioned for slidable insertion through a select one of said cannulas and with a length along a central axis effective to access neoplastic tissue within said peritoneal cavity, having a passageway extending therethrough, and a detector support portion, including a window through which said photon emissions may pass,
- a crystal mount having a crystal receiving portion positioned at said detector support portion in adjacency with said window,
- a crystal having a rearward surface supported upon said crystal receiving portion to position a forward surface thereof in adjacency with said window and responsive to said photon emissions passing through said window to derive an output,
- a transmission assemblage extending from said crystal through said passageway for transmitting said output, and
- a signal treatment and control assembly coupled with said transmission assemblage for receiving and electrically treating said output to provide perceptible output signals representing those photon emissions at predetermined count levels above count levels of said background photon emissions;

visually surveying the colon within said cavity by accessing said camera arrangement thereto through a select one of said access cannulas and detecting any visual indication of neoplastic tissue;

carrying out a radionuclide survey of the colon within said cavity by manipulating said elongate accessing tube of said radiation detection system through a select one of said access cannulas to maneuver said window along and in substantial adjacency with said colon under visualization at said camera arrangement display to detect and differentiate tissue at which said locator has concentrated by correlation of said perceptible output signals to the position of said window with respect to said colon;

carrying out a radionuclide survey of lymph nodes within said cavity by manipulating said elongate accessing tube of said radiation detection system through a select one of said cannulas to maneuver said window under visualization at said camera arrangement display into substantial adjacency with said lymph nodes to detect and locate a lymph node or other metastatic disease at which said locator has concentrated by correlation of said perceptible output signals to the position of said window; and determining the said treatment modality based upon said visual survey of the colon and by said radionuclide surveys of the colon and lymph nodes.

2. The method of claim 1 in which:
said patient is diagnosed prior to said surveys as presenting said neoplastic tissue as primary tumor,
said step for visually surveying the colon is carded out with the absence of a visual indication of neoplastic tissue;
said step for carrying out a radionuclide survey of the colon locates and differentiates said tissue at which said locator has concentrated:
said step for carrying out a radionuclide survey of the lymph nodes locates no lymph node or metastatic disease at which said locator has concentrated; and
then said determination of said treatment modality indicates that a laparoscopically assisted removal of said located and differentiated neoplastic tissue is beneficial as said treatment modality.

3. The method of claim 2 in which:
said patient is diagnosed prior to said surveys as presenting said neoplastic tissue as primary tumor;
said step for visually surveying the colon is carried out in the absence of a visual indication of neoplastic tissue;
said step for carrying out a radionuclide survey of the colon locates and differentiates said tissue at which said locator has concentrated;
said step for carrying out a radionuclide survey of the lymph nodes locates a lymph node at which said locator has concentrated; and
then said determination of said treatment modality indicates that the carrying out an open laparotomy to remove said located and differentiated neoplastic tissue is beneficial as said treatment modality.

4. The method of claim 1 in which:
said patient is diagnosed prior to said surveys as presenting said neoplastic tissue as primary tumor,
said step for visually surveying the colon is carried out with the result of a presence of a visual indication of neoplastic tissue;
said step for carrying out a radionuclide survey of the colon differentiates said tissue at which said locator has concentrated;
said step for carrying out a radionuclide survey of the lymph nodes locates no lymph node or metastatic disease at which said locator has concentrated; and
then said determination of said treatment modality indicates that carrying out a laparoscopically assisted removal of said located neoplastic tissue is beneficial as said treatment modality.

5. The method of claim 1 in which:
said patient is diagnosed prior to said surveys as presenting said neoplastic tissue as primary tumor;
said step for carrying out a radionuclide survey of the colon differentiates said neoplastic tissue at which said locator has concentrated; and
then said determination of said treatment modality indicates that carrying out a laparoscopically assisted removal of said located neoplastic tissue is beneficial as said treatment modality.

6. The method of claim 1 in which:
said patient is diagnosed prior to said surveys as presenting said neoplastic tissue as recurrent tumor;
said step for carrying out a radionuclide survey of lymph nodes locates a lymph node or other metastatic disease at which said locator has concentrated; and
then said determination of said treatment modality indicates a procedure employing surgical resection would not be of benefit to said patient.

* * * * *